(12) United States Patent
Cox et al.

(10) Patent No.: US 9,827,314 B2
(45) Date of Patent: Nov. 28, 2017

(54) EDIBLE COMPOSITIONS WHICH ARE ADAPTED FOR USE BY A COMPANION ANIMAL

(75) Inventors: Edward Russell Cox, Germantown, OH (US); Douglas Joseph Dobrozsi, Loveland, OH (US); Thomas Edward Huetter, West Chester, OH (US); Allan John Lepine, Dayton, OH (US); Susan Ruth Ward, Oregonia, OH (US)

(73) Assignee: Mars, Incorporated, McLean, VA (US)

( * ) Notice: Subject to any disclaimer, the term of this patent is extended or adjusted under 35 U.S.C. 154(b) by 2683 days.

(21) Appl. No.: 10/730,346

(22) Filed: Dec. 8, 2003

(65) Prior Publication Data

US 2005/0123585 A1   Jun. 9, 2005

(51) Int. Cl.

| | |
|---|---|
| *A61K 45/06* | (2006.01) |
| *A23K 1/00* | (2006.01) |
| *A23K 1/175* | (2006.01) |
| *A23K 1/18* | (2006.01) |
| *A61K 33/42* | (2006.01) |
| *A61K 33/34* | (2006.01) |
| *A61K 33/32* | (2006.01) |
| *A61K 33/30* | (2006.01) |
| *A61K 31/28* | (2006.01) |
| *A61K 31/30* | (2006.01) |
| *A61K 31/315* | (2006.01) |
| *A61K 31/32* | (2006.01) |
| *A61K 33/24* | (2006.01) |

(52) U.S. Cl.
CPC .............. *A61K 45/06* (2013.01); *A23K 1/004* (2013.01); *A23K 1/1758* (2013.01); *A23K 1/186* (2013.01); *A23K 1/1853* (2013.01); *A61K 31/28* (2013.01); *A61K 31/30* (2013.01); *A61K 31/315* (2013.01); *A61K 31/32* (2013.01); *A61K 33/24* (2013.01); *A61K 33/30* (2013.01); *A61K 33/32* (2013.01); *A61K 33/34* (2013.01); *A61K 33/42* (2013.01)

(58) Field of Classification Search
None
See application file for complete search history.

(56) References Cited

U.S. PATENT DOCUMENTS

| | | | | |
|---|---|---|---|---|
| 2,859,115 | A | * | 11/1958 | Rivoche ........................ 426/575 |
| 3,422,182 | A | * | 1/1969 | Knapp, Jr. .................... 424/637 |
| 3,899,607 | A | | 8/1975 | Miller et al. |
| 4,039,687 | A | * | 8/1977 | Weyn ............................ 426/62 |
| 4,104,406 | A | | 8/1978 | Stringer et al. |
| 4,145,447 | A | * | 3/1979 | Fisher et al. ................... 426/72 |
| 4,247,562 | A | * | 1/1981 | Bernotavicz ................... 426/72 |
| 4,454,164 | A | | 6/1984 | Gellman et al. |
| 5,000,940 | A | | 3/1991 | Staples et al. |
| 5,000,943 | A | * | 3/1991 | Scaglione et al. ............. 424/57 |
| 5,000,944 | A | | 3/1991 | Prencipe et al. |
| 5,000,973 | A | | 3/1991 | Scaglione et al. |
| 5,011,679 | A | * | 4/1991 | Spanier et al. ................. 424/57 |
| 5,015,485 | A | | 5/1991 | Scaglione et al. |
| 5,047,231 | A | | 9/1991 | Spanier et al. |
| 5,069,903 | A | * | 12/1991 | Stitt ............................. 424/768 |
| 5,094,870 | A | * | 3/1992 | Scaglione et al. ............ 426/549 |
| 5,100,651 | A | | 3/1992 | Boyer |
| 5,114,704 | A | | 5/1992 | Spanier et al. |
| 5,171,603 | A | * | 12/1992 | Singer et al. ................. 426/572 |
| 5,186,964 | A | | 2/1993 | Gierhart et al. |
| 5,296,209 | A | * | 3/1994 | Simone et al. ................. 424/49 |
| 5,296,217 | A | | 3/1994 | Stookey |
| 5,300,289 | A | | 4/1994 | Garlich et al. |
| 5,364,845 | A | * | 11/1994 | Henderson ...................... 514/54 |
| 5,380,530 | A | | 1/1995 | Hill |
| 5,405,836 | A | * | 4/1995 | Richar et al. ................... 514/23 |
| 5,407,661 | A | | 4/1995 | Simone et al. |
| 5,431,927 | A | | 7/1995 | Hand et al. |

(Continued)

FOREIGN PATENT DOCUMENTS

| | | |
|---|---|---|
| EP | 0579333 | 3/1997 |
| GB | 1591406 A | 6/1981 |

(Continued)

OTHER PUBLICATIONS

The Merck Veterinary Manual Eighth Edition, AAFCO Nutrient Requirements for Dogs, National Publishing Inc. Editor Aiello, Copyright 1998, pp. 1626, 1627, 1630, 1631.*
Dzanis. J. Nutr.124 (12): 2535S. 1994.*
Dry Dog Food. http://www.naturalpetmarket.com/category_detail.cfm?categoryid=175&varpageid=999&uplevel=All%20Natural%20Dog%20Food&level=Dry%20Dog%20Food. Archived Jul. 1, 2002. Accessed Oct. 5, 2010.*
Dog's Health. http://55dog.com/doghealth/index.html/. Archived Sep. 30, 2002. Accessed Oct. 6, 2010.*
Natural Balance. http://www.jbpet.com/natural-balance-dry-dog-food-lid-lamb-meal-and-brown-rice-formula,7654.html. Archived Feb. 1, 2001. Accessed Oct. 6, 2010.*

(Continued)

*Primary Examiner* — David J Blanchard
*Assistant Examiner* — Lori K Mattison
(74) *Attorney, Agent, or Firm* — Mars, Incorporated

(57) ABSTRACT

Disclosed herein are a variety of embodiments of compositions and methods which are each adapted for use by a companion animal. In one embodiment, an edible composition comprising an amount of a soluble mineral component is disclosed, wherein the soluble mineral component comprises one or more minerals selected from the group consisting of zinc, manganese, tin, copper, and mixtures thereof, wherein the amount is an effective amount for use as an oral medicament. In further embodiments, a phosphate component is included. The edible compositions are advantageously companion animal foods or supplements. Further disclosed are methods selected from treating oral cavity tartar, oral cavity plaque, periodontal disease, gingivitis, breath odor and combinations thereof comprising orally administering a described composition to a companion animal.

8 Claims, No Drawings

(56) References Cited

U.S. PATENT DOCUMENTS

| | | | |
|---|---|---|---|
| 5,467,741 A | 11/1995 | O'Rourke | |
| 5,501,868 A | 3/1996 | Coolings et al. | |
| 5,618,518 A | 4/1997 | Stookey | |
| 5,879,698 A | 3/1999 | Ellenbogen et al. | |
| 5,904,923 A | 5/1999 | Cyer et al. | |
| 5,904,928 A | 5/1999 | Cyr et al. | |
| 5,919,499 A * | 7/1999 | Lawley | 426/2 |
| 5,922,379 A | 7/1999 | Wang | |
| 6,056,991 A | 5/2000 | Axelrod | |
| 6,060,100 A * | 5/2000 | Koller | 426/315 |
| 6,080,419 A | 6/2000 | Stookey | |
| 6,086,940 A | 7/2000 | Axelrod | |
| 6,093,441 A | 7/2000 | Axelrod | |
| 6,110,521 A | 8/2000 | Axelrod | |
| 6,126,978 A | 10/2000 | Axelrod | |
| 6,156,355 A | 12/2000 | Shields et al. | |
| 6,159,508 A | 12/2000 | Wolf et al. | |
| 6,159,516 A | 12/2000 | Axelrod et al. | |
| 6,159,530 A * | 12/2000 | Christiansen et al. | 426/656 |
| 6,177,107 B1 | 1/2001 | Watson et al. | |
| 6,180,161 B1 | 1/2001 | Axelrod | |
| 6,227,420 B1 | 5/2001 | Jepson | |
| 6,228,418 B1 | 5/2001 | Gluck et al. | |
| 6,238,726 B1 | 5/2001 | Fischer | |
| 6,254,920 B1 | 7/2001 | Brunner | |
| 6,265,011 B1 | 7/2001 | Kelly et al. | |
| 6,265,438 B1 | 7/2001 | Steward | |
| 6,274,182 B1 | 8/2001 | Axelrod et al. | |
| 6,277,435 B1 * | 8/2001 | Lacombe et al. | 426/646 |
| 6,350,485 B2 * | 2/2002 | Brunner | 426/656 |
| 6,379,725 B1 | 4/2002 | Wang et al. | |
| 6,455,083 B1 | 9/2002 | Wang | |
| 6,517,877 B2 | 2/2003 | Gannon | |
| 6,841,178 B2 | 1/2005 | Cupp et al. | |
| 6,904,870 B2 | 6/2005 | Russell-Maynard et al. | |
| 6,911,224 B1 | 6/2005 | May et al. | |
| 6,932,980 B1 | 8/2005 | Sayre et al. | |
| 7,390,520 B2 | 6/2008 | Dempsey et al. | |
| 9,415,067 B2 | 8/2016 | Jones et al. | |
| 2001/0002272 A1 * | 5/2001 | Brunner | 426/656 |
| 2001/0043941 A1 | 11/2001 | Huatan et al. | |
| 2002/0090444 A1 | 7/2002 | Cupp et al. | |
| 2002/0119224 A1 * | 8/2002 | Axelrod et al. | 426/132 |
| 2002/0119241 A1 | 8/2002 | Speck et al. | |
| 2003/0072841 A1 | 4/2003 | Rajaiah et al. | |
| 2003/0077254 A1 * | 4/2003 | Ramaekers | 424/93.3 |
| 2003/0092019 A1 | 5/2003 | Meyer et al. | |
| 2003/0175387 A1 * | 9/2003 | English | 426/94 |
| 2003/0219516 A1 | 11/2003 | Pater et al. | |
| 2004/0037943 A1 | 2/2004 | Saylock et al. | |
| 2004/0037944 A1 | 2/2004 | Cupp et al. | |
| 2004/0076735 A1 * | 4/2004 | Lacombe et al. | 426/641 |
| 2004/0156883 A1 | 8/2004 | Brown et al. | |
| 2004/0234654 A1 | 11/2004 | Levin | |
| 2005/0084563 A1 * | 4/2005 | Cupp et al. | 426/2 |
| 2005/0123585 A1 | 6/2005 | Cox et al. | |
| 2006/0147962 A1 | 7/2006 | Jones et al. | |
| 2007/0009899 A1 | 1/2007 | Mounts | |
| 2007/0134370 A1 | 6/2007 | Umeda et al. | |
| 2008/0226766 A1 | 9/2008 | Fretwell et al. | |
| 2010/0278938 A1 | 11/2010 | Jones et al. | |
| 2012/0021928 A1 | 1/2012 | Lindblad-Toh et al. | |
| 2014/0093584 A1 | 4/2014 | Jones et al. | |

FOREIGN PATENT DOCUMENTS

| | | | |
|---|---|---|---|
| JP | H10201428 | | 8/1998 |
| JP | 2001-299234 A | | 10/2001 |
| WO | 9508641 | | 3/1995 |
| WO | 9731011 | | 8/1997 |
| WO | WO 99/60866 A1 | | 12/1999 |
| WO | WO 00/30456 A1 | | 6/2000 |
| WO | WO 00/47049 A1 | | 8/2000 |
| WO | WO 01/17366 | * | 3/2001 ............. A23K 1/16 |
| WO | WO0117364 | * | 3/2001 ............. A23K 1/00 |
| WO | WO 01/70043 | | 9/2001 |
| WO | 03/033734 | | 4/2003 |
| WO | WO 2004/014143 A | | 2/2004 |
| WO | 2004113570 | | 12/2004 |
| ZA | 9905557 | * | 6/2000 |

OTHER PUBLICATIONS

Hale. Journal of Veterinary Dentistry. 1998. vol. 15(2):79-83. Abstract Only.*
Royal Canin. http://www.petco.com/product/10844/Royal-Canin-MINI-Canine-Health-Nutrition-Yorkshire-28.aspx. Published on Aug. 15, 2003. Accessed Oct. 6, 2010.*
Kirk et al.., "Encyclopedia of Chemical Technology", vol. 15: 232-276 1965.
Kleinberg et al., Department of Oral Biology & Pathology, School of Dental Medicine, State University of New York, Stony Brook, New York, USA 11794-8702.
Guggenheim et al., "Validation of an In Vitro Biofilm Model of Supragingival Plaque", 80 (1): 363-370, 2001.
Xia, "High-Quality Dog Breeding Manual", Hebei Science & Technology Press, 1st Ed., Jan. 31, 2009 (7 pages).
Poulsen, et al., "X-Linked Recessive Menkes Disease: Carrier Detectoin in the Case of a partial Gene Deletion", Clinical Genetics, 2002, vol. 62, pp. 440-448.
Proschowsky, et al., "Microsatellite Marker C04107 as a Diagnostic Marker for Copper Toxicosis in the Danish Population of Bedlington Terriers", Acta. Vet. Scand., 2000: 41(4):345-50.
Shih, et al., "Chronic Hepatitis in Labrador Retrievers: Clinical Presentation and Prognostic Factors", Journal of Veterinary Internal Medicine, Jan. 2007, 21(1), pp. 33-39.
Shimizu, et al., "Treatment and Management of Wilson's Disease", Pediatrics International, 41: 419-422, 1999.
Spee, et al., "Copper Metabolism and Oxidative Stress in Chronic Inflammatory and Cholestatic Liver Diseases in Dogs", Journal of Veterinary Internal Medicine, Sep. 2006, 20(5), pp. 1085-1092.
Spee, et al., "Differential Expression of Copper-Associated and Oxidative Stress Related Proteins in a New Variant of copper Toxicosis in Doberman Pinschers", Comparative Hepatology, 2005, 4:3, pp. 1-13.
Stuehler, et al., "Analysis of the Human Homologue of the Canine Copper Toxicosis Gene MURR1 in Wilson Disease Patients", Journal of Molecular Medicine, vol. 82, No. 9, Sep. 2004, pp. 629-634.
Thornburg, "A Perspective on Copper and Liver Disease in the Dog", J. Vet. Diagn. Invest, Dec. 31, 2000, vol. 12, pp. 101-110.
Van De Sluis, et al., "Genetic Mapping of the Copper Toxicosis Locus in Bedlington Terriers to Dog Chromosome 10, in a Region Syntenic to Human Chromosome Region 2p13-p16", Human Molecular Genetics, 1999, vol. 8, No. 3, pp. 501-507.
Van De Sluis, et al., "Genetic Mapping of the Copper Toxicosis Locus in BedlingtonTerriers to Dog Chromosome 10, in a Region Syntenic to Human Chromosome Region 2P13-P16", Human Molecular Genetics, Oxford University Press, Surrey, GB, vol. 8, No. 3, Mar. 1999, 501-507.
Van De Sluis, et al., "Identification of a New Copper Metabolism Gene by Positional Cloning in a Purebred Dog Population", Human Molecular Genetics, 11(2): 165-173, 2002.
Van De Sluis, et al., "Refined Genetic and Comparative Physical Mapping of the Canine Copper Toxicosis Locus", Mammalian Genome, 11, 455-460 (2000).
Wijmenga, et al., "Molecular regulation of copper excretion in the liver", Proceedings of the Nutrition Society, 63 (2004), pp. 31-39.
Wu, et al., "Canin Models for Copper Homeostasis Disorders", International Journal of Molecular Sciences, 2016, vol. 17, No. 196, 14 pgs.
Xiaoqing, et al., "Application of D135301 Label in Diagnosis of Wilson Disease", Journal of Clinical Pediatrics, 20(10):614-616, Oct. 20, 2002.
Yuxin, et al., "A Preliminary Study of the Chinese P-Type Copper Transporting ATPase Gene Mutation", Journal of Fudan University, Natural Science Edition, 36(5):517-523, Oct. 31, 1997.

(56) References Cited

OTHER PUBLICATIONS

Yuzbasiyan-Gurkan, et al., "Linkage of Microsatellite Marker to the Canine Copper Toxicosis Locus in Bedlington Terriers", Am. J. Vet. Res. 58:23-27 (1996).
Yuzbasiyan-Gurkan, et al., "Microsatellite Markers for the Canine Genome", Canis familiaris STS microsatellite marker, Apr. 14, 1996, retrieved from EBI Database accession No. L7759, XP002248976 Abstract, 1 pg.
Zhao, "Human BAC Ends", Nucleic Acids Research, 2000, vol. 28, No. 1, pp. 129-132.
Zhi-Ying, et al., "Mutation analysis of 218 Chinese patients with Wilson disease revealed no correlation between the canine copper toxicosis gene MURR1 and Wilson disease", J. Mol. Med., 84(2006), pp. 438-442.
Chinese Search Report dated Mar. 8, 2013, issued during prosecution of China Patent Application No. 2010800254455., 12 pgs.
PCT International Report on Patentability issued in International Application No. PCT/GB2009/002355, dated Apr. 14, 2011., 12 pgs.
PCT International Search Report and Written Opinion issued in International Application No. PCT/GB2008/003351, dated May 27, 2009, 15 pgs.
PCT International Report on Patentability issued in International Application No. PCT/GB2008/003351, dated Apr. 7, 2010., 16 pgs.
Force Dog Food—Gluten Free, The Honest Kitchen, product Sheet, downloaded 2014, 2 pgs.
Flint River Ranch Super Premium Dry Water Kibble Dog Food, product sheet, Downloaded 2014, 3 pgs.
Copper Content in Dog Foods (http:rottndobie.tripod.com/coppercontent.html, Nov. 2004), 4 pgs.
Great life Grain/Potato Free Dog Food as evidenced by Great life Rubicon (www.healthyplanetrx.com/Great-Life-Rubicon-for-dogs-p, Jul. 5, 2006), 5 pgs.
Search Report issued in United Kingdom Application No. GB1120989.7, dated Mar. 30, 2012, 5 pgs.
PCT International Search Report issued in International Application No. PCT/GB2009/002355, dated Nov. 26, 2009, 6 pgs.
PCT International Search Report and Written Opinion issued in International Application No. PCT/GB2010/000703, dated Jun. 16, 2010, 8 pgs.
PCT International Report on Patentability issued in International Application No. PCT/GB2010/000703, dated Jun. 16, 2010., 9 pgs.
"Burns: Developed by a Veterinary Surgeon. The Holistic Approach to Health and Nutrition", Burns Pet Nutrition Ltc., product brochure, available online at http://www.burns-pet-nutrition.co.uk.colour_brochure2006_small.pdf, 9 pgs.
"CanineHD BeadChip", Illumina, Data Sheet: DNA Genotyping, 170K Chip, 2010, 4 pgs.
"dbSNP Short Genetic Variations", Database Medline US National Library of Medicine (NLM), Bethesda, MD, US, Feb. 2, 2005, XP002696928, Database accession no. rs22088177, 2 pgs.
"Dietary Survey Study, Jun. 5, 2010; Utrecht University", 2 pgs.
"English Translation of Japanese Office Action dated Sep. 2, 2014, JP Appl. No. 2012-504068", 9 pgs.
"Health and Related Issues", Internet <URL:http://homepages.rootsweb.ancestry.com/oldmill/chelseaBB/HealthPage. htm>., Aug. 27, 2013, 2-5.
"Hill's Pet Nutrition Hills Prescription L/D", Hill's Pet Nutrition, Aug. 26, 2015, 2 pgs.
"Nutrient Analysis", Hill's Pet Nutrition, Inc., Jan. 19, 1999, 8 pgs.
"Premium Nutrition for Dogs, Natures Recipe Large Breed Product Description", Del Monte: Natures Recipe available online at http://www.naturesrecipe.com/DogProductDisplay.aspx?p=Dogs/Breed_LargeBreed, 2007, 4 pgs.
"Premium Nutrition for Dogs, Terrier Dogs Canine Recipe Product Description", Del Monte Nature's Recipe, available online at http://www.naturesrecipe.com/dogproductdisplay.aspx?p=Dogs/Breed_dryTerrier, 2006, 4 pgs.

"Prescription Diet Canine l/d (liver disease)", Hills Pet Nutrition, availlable online at http://www.hillspet.com/media/WEURG/product/prodkeyPDF/en.pdf, accessed Jan. 30, 2008, 1 pg.
"Regenerative and Fibrotic Pathways in Canine Liver Disease", Faculty of Veterinary Medicine, 2006, 26 pgs.
"Small Animal Clinical Nutrition", Mark Morris Institute, 2000, Ed. 4th, 32 pgs.
"The Best Foods for Dogs With Chronic Active Hepatitis", A Dog's Life Photography & Art [online], Jun. 29, 2010, [retrieved on Aug. 21, 2013], Internet <URL: http://phoenixdogphotography.com/2010/06/the-best-foods-for-dogs-with-ahronic-active-hepatitis/>, 4 pgs.
"The Hill's Key to Clinical Nutrition", Hill's Pet Nutrition, Inc., 1999, 4 pgs.
"Trophy Pet Foods: Trophy Premium Hypo-Allerfenic food", Trophy Pet Foods, available online at http://www.trophypeffoods.co.uk/products/premiumdog.htm, accessed Jan. 30, 2008, 3 pgs.
"University Study Shows Dogs have a Lot to Gain when they Lose Weight", GoodNewsforPets.com, recorded on May 12, 2007, Internet Archive Wayback Machine, searched http://goodnewsforpets.com/news/archive/Research/041300_weight_study_html, Internet <URL:http://web.archive.org/web/20070512095423/http://www.goodnewsforpets.com/new, 2-4.
"Whole Dog Journal's Food List", Little Dog & Girl on the Prairie [online], Jun. 27, 2007, [retrieved on Aug. 21, 2013], internet <URL:http://blog.livedoor.jp/urea/archives/51627947.html>, 4 pgs.
Allen, et al., "Tetramine Cupruretic Agents: A Comparison in Dogs", Am. J. Vet. Res., 48(1): 28-30, 1987.
Bergstrom, et al., "The Pharmacokinetics of Penicillamine in a Female Mongrel Dog", Journal of Pharmacokinetics and Biopharmaceutics, Feb. 6, 1981, vol. 9, No. 5, pp. 603-621, Plenum Publishing Corporation.
Breen, et al., "Chromosome specific single locus FISH probes allow anchorage of a 1800 marker integrated radiation-hydrid/linkage map of the domestic dog genome to all chromosomes", Genome Res., Oct. 2001, 11(10):1784-1795.
Coronado, et al., "New Haplotypes in the Bedlington Terrier Indicate Complexity in Copper Toxicosis", Mammalian Genome, 2003, vol. 14, pp. 483-491.
Coronado, et al., "Polymorphisms in canine ATP7B: Candidate Modifier of Copper Toxicosis in the Bedlington terrier", Veterinary Journal, 177(2):293-296, 2008.
Debenham, "Physical and Linkage Mapping of the Canine Phosphate Carrier (SLC25A3) and Apoptotic Activating Factor (APAF1) Genes to Canine Chromosome 15", Canis familiar's microsatellite, Nov. 24, 2000, retrieved from EBI Dtabase Accession No. AJ299437, Abstract XP002248980, 1 pg.
Dias Neto, et al., "Shotgun Sequencing of the Human Transcriptome with Ore Expressed Sequence Tags", Homo sapien cDNA mRNA sequence, Jan. 12, 2001, retrieved from EBI Database accession No. BF49428, Abstract No. XP002248981, 1 pg.
Dunn, et al., "Mouse Whole Genome Scaffolding with Paired End Reads from 10kb Plasmid Inserts", Mouse Library Mus Musculus Genomic Clone, Feb. 18, 2001, retrieved from EBI Database Accession No. Az759124, XP002248979 Abstract, 1 pg.
Fieten, et al., "The Menkes and Wilson disease genes counteract in copper toxicosis in Labrador retrievers: a new canine model for copper-metabolism disorders", Disease Models and Mechanisms, vol. 9, pp. 25-38, 2016.
Friedman, et al., "Isolation of a Ubiquitin-like (UBL5) Gene from a Screen Identifying Highly Expressed adn Conserved Iris Genes", Genomics, Dec. 31, 2001, vol. 71, pp. 252-255.
Fuentealba, et al., "Animal Models of Copper-Associated Liver Disease", Comparative Hepatology, Apr. 3, 2003, vol., 2, No. 1, 12 pgs.
Haywood, et al., "Copper Toxicosis in the Bedlington Terrier: A Diagnostic Dilemma", Journal of Small Animal Practice, Blackwell Scientific Publications, Apr. 1, 2001, 42(4), pp. 181-185.
Hirschhorn, et al., Genetics in Medicine, vol. 4, No. 2, pp. 45-61, Mar. 2002.
Hoffman, et al., "Copper-Associated Chronic Hepatitis in Labrador Retrievers", Journal of Veterinary Internal Medicine, Jul. 2006, 20(4), pp. 856-861.

(56) References Cited

OTHER PUBLICATIONS

Hyun, et al., "Evaluation of Halotypes Associated with Copper Toxicosis in Bedlington Terriers in Australia", American Journal of Veterinary Research, 2004, vol. 65, pp. 1573-1579.
Ioannidis, et al., "Replication Validity of Genetics Association Studies", Nature Genetics, vol. 29, pp. 306-309, Nov. 2001.
Madsen, et al., "Zebrafish Mutants Calamity and Catastrophy Define Critical Pathways of Gene-Nutrient Interactions in Developmental Copper Metabolism", PLOS Genetics, 4(11):1-11, 2008.
Murphy, et al., Genbank Accesion No. AY011436, Feb. 7, 2001, 2 pgs.
Noaker, et al., Javma, vol. 214, No. 10, pp. 1502-1506, 1999.
Dias Neto, et al., "Shotgun Sequencing of the Human Transcriptome with ORF Expressed Sequence Tags", Homo sapien cDNA mRNA sequence, Jan. 12, 2001, retrieved from EBI Database accession No. BF49428, Abstract No. XP002248981, 2 pgs.

\* cited by examiner

EDIBLE COMPOSITIONS WHICH ARE ADAPTED FOR USE BY A COMPANION ANIMAL

FIELD OF THE INVENTION

The present invention relates to compositions and methods which are useful for the treatment of conditions associated with the oral cavity of a companion animal. In particular, the invention relates to the use of defined edible compositions which are adapted for use by the companion animal.

BACKGROUND OF THE INVENTION

Plaque is initiated when bacteria forms a proteinaceous film on the surface of teeth. The adherent bacteria metabolize dietary constituents and reproduce and aggregate to form the tenacious deposit known as plaque. Plaque generally consists of bacteria, bacterial end products such as polysaccharides, inorganic salts and salivary proteins. Plaque bacteria ferment dietary carbohydrates to organic acids which demineralize enamel resulting in tooth decay.

Calculus and tartar are essentially plaque that has been mineralized with calcium phosphate salts. As calculus hardens to tartar, it tends to stain noticeably due to adsorption of dietary chromagens. In addition to their unattractive appearance, these deposits at the gum line are a contributing source of gingivitis and periodontal disease. Besides the hygienic and health problems that result, research has shown that the primary source of bad breath is the retention and subsequent degradation of dead cellular material sloughed off continuously by the normal, healthy oral cavity.

The initiation of plaque or growth of calculus and tartar presents a particular challenge in companion animals, such as dogs or cats, wherein the oral cavities and teeth of such animals may not be cleaned on a regular basis, or even at all. As such, issues such as tartar and plaque, breath malodor, and the like are particularly troublesome. Even further, conventional methods utilized by humans to clean the oral cavity, such as prophylactic and therapeutic treatment by a dental professional or even regular tooth brushing or flossing, is impractical or difficult with all companion animals. Still further, foods or other orally available compositions have only recently been investigated as potential tools for approaching these issues. These issues not only compromise the oral health of the companion animal, but the systemic health as well since poor oral health may lead to systemic infection or other issues. As such, there remains a significant need to provide advances in the treatment of oral health of the companion animal.

Recently, polyphosphates or other phosphate components have been included as part of a companion animal diet in order to address the foregoing issues. For example, IAMS and EUKANUBA foods, commercially available from The Iams Company, Dayton, Ohio) which are adapted for certain companion animals currently provide phosphate components, and are designed for improvements in oral health. Opportunities are still available for further improvements. However, many approaches utilized for human oral health may not be readily adaptable for companion animals due to a variety of reasons, including organoleptic needs, reduction in efficacy upon combination with other components, and the like.

The present invention utilizes a mineral component as part of a composition adaptable for use by a companion animal. The mineral component is provided in a variety of embodiments, which have been designed by the present inventors to reduce the issues presented by certain minerals such as zinc, copper, tin, and manganese. For example, the inventors have discovered that the mineral component may be provided in compositions adapted for companion animal use, and that other preferred executions may be designed to avoid issues such as complexation with phosphate and unacceptable flavor. These and other benefits of the present invention are described herein.

SUMMARY OF THE INVENTION

The present invention is directed to a variety of embodiments of compositions and methods which are each adapted for use by a companion animal.

In one embodiment, the invention is directed to an edible composition comprising an amount of a soluble mineral component, wherein the soluble mineral component comprises two or more minerals selected from the group consisting of zinc, manganese, tin, copper, and mixtures thereof, wherein the amount is an effective amount for use as an oral medicament. In another embodiment, the invention is directed to an edible composition comprising:
  (a) an amount of a soluble mineral component, wherein the soluble mineral component comprises one or more minerals selected from the group consisting of zinc, manganese, tin, copper, and mixtures thereof; wherein the amount is an effective amount for use as an oral medicament; and
  (b) a further amount of a phosphate component, wherein the further amount is an effective amount for use as an oral medicament;
wherein the edible composition is selected from the group consisting of companion animal foods companion animal supplements, and combinations thereof, wherein the companion animal supplement is not a chew.

In yet another embodiment, the invention is directed to an edible composition comprising:
  (a) an amount of a mineral component comprising one or more minerals selected from the group consisting of zinc, manganese, tin, copper, and mixtures thereof, wherein the amount is an effective amount for use as an oral medicament, and wherein at least a portion of the mineral component is coated on the surface of the edible composition;
  (b) a further amount of a phosphate component, wherein the further amount is an effective amount for use as an oral medicament;
wherein the edible composition is a companion animal chew.

In yet another embodiment, the invention is directed to an edible composition comprising:
  (a) an amount of a mineral component comprising a mineral selected from the group consisting of zinc, manganese, tin, copper, and mixtures thereof, wherein the amount is an effective amount for use as an oral medicament; and
  (b) a further amount of a phosphate component, wherein the further amount is an effective amount for use as an oral medicament, and wherein at least a portion of the phosphate component is coated on the surface of the edible composition;
wherein the edible composition is a companion animal chew.

In yet another embodiment, the invention is directed to an edible composition comprising:
  (a) an amount of a mineral component comprising a mineral selected from the group consisting of manganese, tin, copper, and mixtures thereof, wherein the amount is an effective amount for use as an oral medicament;

(b) a further amount of a phosphate component, wherein the further amount is an effective amount for use as an oral medicament;

wherein the edible composition is a companion animal chew.

The invention is further directed to methods selected from treating oral cavity plaque, oral cavity tartar (defined herein as including calculus), periodontal disease, gingivitis, breath odor and combinations thereof comprising orally administering a composition provided herein to the companion animal.

Each embodiment is adapted for use by a companion animal.

DETAILED DESCRIPTION OF THE INVENTION

Various documents including, for example, publications and patents, are recited throughout this disclosure. All such documents are hereby incorporated by reference. The citation of any given document is not to be construed as an admission that it is prior art with respect to the present invention.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the features or embodiments as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

The present invention is directed to compositions, kits, and methods which are adapted for use by companion animals. As used herein, "companion animal" means a domestic animal. Preferably, "companion animal" means a domestic dog, cat, rabbit, ferret, horse, cow, or the like. More preferably, "companion animal" means a domestic dog or cat, particularly a domestic dog.

The term "effective amount" as described herein, will be readily determinable by the ordinarily skilled artisan. As used herein, the term "effective amount," with reference to a specific component, means that amount of the component sufficient to provide a significant improvement of the relevant treatment in a companion animal, yet low enough to avoid adverse effects (such as toxicity, irritation, or allergic response), commensurate with a reasonable benefit/risk ratio when used in the manner of the present invention. The specific "effective amount" may vary with such factors as the particular condition being treated, whether the administered composition is ingested frequently or sporadically, the nature of concurrent therapy (if any), the specific dosage form to be used (e.g., food, biscuit, chew), and the like.

Compositions of the Present Invention

The compositions herein are adapted for use by a companion animal. In this respect, as will be well understood by the ordinarily skilled artisan, the primary use of the compositions described herein is for companion animal use and the compositions are therefore formulated as such.

The present compositions are, in the most advantageous embodiments, nutritionally desirable, stable, possess the ability to sequester calcium, inhibit bacterial growth, inhibit plaque, inhibit tartar (defined herein as including calculus), improve malodor of the oral cavity, and/or the like. The invention is further advantageous for the inhibition of periodontal disease, gingivitis, breath odor, and the like.

The various embodiments described herein each comprise a soluble mineral component. As used herein, the term "soluble" with respect to the mineral component means that at least about 50% of the mineral component, by weight of the mineral component, dissolves in a sample of water (in an amount typically present during mastication) at ambient temperature. Optionally, the term "soluble" with respect to the mineral component means that at least about 75%, or at least about 90%, of the mineral component, again by weight of the mineral component dissolves in this sample of water (in an amount typically present during mastication) at ambient temperature.

The composition comprises an amount of the soluble mineral component which is an effective amount for use as an oral medicament, as has been defined herein above. As an example, the composition may optionally comprise at least about 0.01%, or at least about 0.02%, or at least about 0.05%, or at least about 0.1%, or at least about 0.15% of the mineral component, by weight of the composition. As a further example, the composition may optionally comprise from about 0.01% to about 10%, or from about 0.02% to about 5%, or from about 0.05% to about 5%, or from about 0.1% to about 2%, or from about 0.15% to about 1%, of the mineral component, by weight of the composition. Specific illustrative amounts of each mineral which may be utilized in the mineral component are described below.

The soluble mineral component comprises one or more minerals selected from zinc, manganese, tin, copper, and mixtures thereof. Various embodiments described herein may comprise two or more, or three, or all four of these minerals. Moreover, the minerals from which selections may be drawn may be modified, for example wherein the minerals are selected from manganese, tin, copper, and mixtures thereof. Each of these minerals, including exemplary sources and amounts, are described as follows:

The soluble mineral component may comprise zinc. Sources of zinc which will contribute to a soluble mineral component will be well-known to those of ordinary skill in the art. Illustrative sources of zinc include zinc sulfate, zinc gluconate, zinc chloride, zinc citrate, zinc lactate, zinc malate, zinc tartrate, and mixtures thereof. Zinc sulfate monohydrate is a particularly preferred zinc source. Zinc citrate may impart enhanced palatability relative to certain other zinc sources due to chelation with the citrate. Wherein the composition comprises zinc, the composition may optionally comprise at least about 0.001% zinc ion, at least about 0.01% zinc ion, at least about 0.05% zinc ion, or at least about 0.07% zinc ion, or at least about 0.1% zinc ion, by weight of the composition. As a further example, wherein the composition comprises zinc, the composition may optionally comprise from about 0.001% to about 1%, or from about 0.005% to about 0.75%, or from about 0.05% to about 0.5%, or from about 0.1% to about 0.4% zinc ion, all by weight of the composition.

The soluble mineral component may comprise tin. Sources of tin which will contribute to a soluble mineral component will be well-known to those of ordinary skill in the art. Illustrative sources of tin include tin lactate, tin gluconate, tin acetate, tin sulfate, tin malate, and mixtures thereof. Wherein the composition comprises tin, the composition may optionally comprise at least about 0.0001% tin ion, at least about 0.0005% tin ion, or at least about 0.001% tin ion, or at least about 0.0015% tin ion, by weight of the composition. As a further example, wherein the composition comprises tin, the composition may optionally comprise from about 0.0001% to about 0.5%, or from about 0.0005% to about 0.1%, or from about 0.001% to about 0.05%, or from about 0.001% to about 0.25% tin ion, all by weight of the composition.

The soluble mineral component may comprise copper. Sources of copper which will contribute to a soluble mineral component will be well-known to those of ordinary skill in the art. Illustrative sources of copper include copper chloride, copper gluconate, copper sulfate, copper bisglycinate, copper lactate, copper malate, copper acetate, copper citrate, copper tartrate, and mixtures thereof. Copper sulfate pentahydrate is particularly preferred herein. Wherein the composition comprises copper, the composition may optionally comprise at least about 0.0005%, or at least about 0.01%, or at least about 0.015%, or at least about 0.02% copper ion, all by weight of the composition. As a further example, wherein the composition comprises copper, the composition may optionally comprise from about 0.0005% to about 0.5%, or from about 0.0005% to about 0.1%, or from about 0.01% to about 0.1%, or from about 0.015% to about 0.05%, or from about 0.02% to about 0.25% copper ion, all by weight of the composition.

The soluble mineral component may comprise manganese. Sources of manganese which will contribute to a soluble mineral component will be well-known to those of ordinary skill in the art. Illustrative sources of manganese include manganese chloride, manganese sulfate, manganese gluconate, manganese acetate, manganese malate, manganese tartrate, manganese citrate, manganese lactate, manganese glycinate, and mixtures thereof. Manganese sulfate monohydrate is particularly preferred herein. Wherein the composition comprises manganese, the composition may optionally comprise at least about 0.0001% manganese ion, or at least about 0.001%, or at least about 0.01%, or at least about 0.015%, or at least about 0.02% manganese ion, by weight of the composition. As a further example, wherein the composition comprises manganese, the composition may optionally comprise from about 0.0001% to about 1%, or from about 0.001% to about 0.5%, or from about 0.01% to about 0.5%, or from about 0.05% to about 0.4% manganese ion, all by weight of the composition.

In an optional embodiment herein, at least a portion of the mineral component is coated on the surface of the composition. Consistent with this embodiment, the inventors have discovered that the mineral component can be provided on the surface of the composition without substantial compromise in the organoleptic, or other key properties of the composition. As such, the compositions are satisfactorily administered to the companion animal while providing optimized efficacy since the mineral component is readily available and quickly solubilized in the oral cavity of the companion animal. Dosage forms such as foods and supplements, including biscuits or chews, are desirable with this embodiment. In a further preferred embodiment at least about 50% of the mineral component, or at least about 75% of the mineral component, or at least about 90% of the mineral component, or at least about 95% of the mineral component, all by weight of the mineral component, is coated on the surface of the composition.

In another optional embodiment herein, at least a portion of the mineral component is integrated within the edible composition. This is particularly desirable wherein the composition is in a dosage form which is a companion animal chew, wherein the animal chews the composition over an extended period of time. The inventors have discovered that, in this embodiment, efficacy is enhanced through availability of the mineral component over an extended period of time.

In one embodiment herein, the compositions comprise a mineral component and a phosphate component. Unexpectedly, the inventors herein have demonstrated that the benefits of compositions containing both of these components may be superior to those benefits achieved by either component alone, thereby resulting in a truly synergistic benefit. This discovery has been found as not limited to the chain length of phosphate utilized; rather, the benefits of the phosphate component may be enhanced when combined with mineral component, regardless of chain length. The composition may optionally comprise an amount of a phosphate component which is an effective amount for use as an oral medicament, as has been defined herein above. Preferably, unlike the complexes described in U.S. Pat. No. 5,000,944, the mineral component and the phosphate component, or any individual components thereof, are not present as a complex in the composition.

The phosphate component comprises a component which contains at least 2 phosphorous atoms. Illustrative compounds which may be utilized as the phosphate component include pyrophosphates, polyphosphates, or mixtures thereof. Kirk & Othmer, *Encyclopedia of Chemical Technology*, $2^{nd}$ Ed., Vol. 15 (1965), pp. 232 to 276, discloses a number of water-soluble inorganic pyrophosphate salts.

In one embodiment herein, at least a portion of the phosphate component is a pyrophosphate. For example, inorganic pyrophosphates such as alkali metal pyrophosphates including sodium acid pyrophosphate (SAPP) and tetrapotassium pyrophosphate (TKPP) may be utilized. Illustrative examples of SAPP include SAPP having a molecular weight of about 222. Also useful may be a tetraalkali metal pyrophosphate such as tetralithium pyrophosphate. Examples of dialkaline metal pyrophosphates are dicalcium pyrophosphate, dibarium pyrophosphate, and dimagnesium pyrophosphate. Trialkali metal monoacid pyrophosphates such as trisodium hydrogen pyrophosphate may also be used.

In another embodiment, at least a portion of the phosphate component is a polyphosphate. As will be readily understood in the art, as the chain length of the polyphosphate increases, the polyphosphate is provided as multiple length species having an average chain length. Polyphosphates may also be utilized herein, such as those polyphosphates having an average chain length of 3 or greater. Examples include tripolyphosphates such as sodium tripolyphosphate (STPP), SODAPHOS (average chain length of 7), HEXAPHOS (average chain length of 13) (commercially available from FMC Corporation), other hexametaphosphate (such as, average chain length of 21), and sodium acid metaphosphate. Illustrative examples of hexametaphosphate include sodium hexametaphosphate or potassium hexametaphosphate having a molecular weight of about 2200.

The phosphate component may be provided wherein at least a portion of the phosphate component is coated on the surface of the composition, at least a portion of the phosphate component is integrated within the composition, or both.

Particularly preferred embodiments include those companion animal food compositions (for example, biscuits or chews) wherein the at least a portion of the mineral component is coated on the surface of the composition and at least a portion of the phosphate component is integrated within the composition, or at least a portion of the phosphate component is coated on the surface of the composition and at least a portion of the mineral component is integrated within the composition, or wherein at least a portion of both the mineral and phosphate components are coated on the surface of the composition, or wherein at least a portion of both the mineral and phosphate components are integrated within the composition. Other particularly preferred embodiments include those companion animal supplement compositions (for example, biscuits or chews) wherein the at least a portion of the mineral component is coated on the surface of the composition and at least a portion of the phosphate component is integrated within the composition, or at least a portion of the phosphate component is coated on the surface of the composition and at least a portion of the mineral component is integrated within the composition, or wherein at least a portion of both the mineral and phosphate components are coated on the surface of the composition, or wherein at least a portion of both the mineral and phosphate components are integrated within the composition.

As an example, the composition may optionally comprise at least about 0.05%, or at least about 0.1%, or at least about 0.2%, or at least about 0.5%, or at least about 1% of the phosphate component, by weight of the composition. As a further example, the composition may optionally comprise from about 0.05% to about 10%, or from about 0.1% to about 5%, from about 0.2% to about 4%, or from about 0.5% to about 4% of the phosphate component, by weight of the composition.

The compositions of the invention may be provided as any of a variety of dosage forms, including food compositions or supplement compositions which are adapted for companion animal use. Examples will include foods (e.g., dog foods, cat foods, and the like) and supplements (e.g., biscuits, chews, and the like).

Optionally, the composition herein may be a food composition such as a dry composition (for example, kibble), semi-moist composition, wet composition, or any mixture thereof. Dry compositions, or those which are semi-moist, are particularly preferred when used in accordance with the present invention. Companion animal foods are particularly well-known in the art.

Alternatively or additionally, the composition is a supplement, such as a companion animal chew or companion animal biscuit, or other treat for a companion animal, such as cat or dog treats. Companion animal biscuits, such as dog biscuits, are well known in the art. Examples of biscuits include those described in the following documents: U.S. Pat. Nos. 5,405,836; 5,000,940; 5,000,943; 5,000,973; 5,094,870; and 5,015,485. Chews are also widely known, and can be provided in a variety of forms, including those prepared by baking, extrusion, injection molding, transfer molding, and/or compression molding. Typically, the texture, pliancy and consistency of the molded articles encourage gnawing. Gnawing action allows the companion animal to softly penetrate the chewable pet toy, promoting clean, healthy teeth and fresh breath. Chews are typically consumed by the companion animal over a period of at least about 1 minute, or at least about 2 minutes, or at least about 5 minutes, or at least about 10 minutes, or at least about 30 minutes. Examples of typical chews are disclosed in the following documents: U.S. Pat. Nos. 6,379,725; 6,455,083; 5,922,379; 6,265,011; 6,517,877; 6,274,182; 6,056,991; 6,159,516; 6,086,940; 6,110,521; 6,093,441; 6,126,978; 6,180,161; 6,277,420; 6,238,726; 5,431,927; 6,228,418 and 5,296,209 and U.S. patent application Publication Nos. 2002/0119241; 2002/0119224; 2001/0043941; and 2002/0090444.

In one embodiment, the composition is nutritionally balanced. As used herein, the term "nutritionally balanced," with reference to the composition, means that the composition has known required nutrients to sustain life in proper amounts and proportion based on recommendations of recognized authorities in the field of companion animal nutrition. Wherein the composition is a food composition, it is most preferably nutritionally balanced.

The compositions herein may optionally comprise one or more further components. Other components are beneficial for inclusion in the compositions used herein, but are optional for purposes of the invention. For example, the compositions herein advantageously comprise a source of protein, carbohydrate, and/or fat, preferably protein, carbohydrate, and fat.

Crude protein material may comprise vegetable proteins such as soybean, cottonseed, and peanut, or animal proteins such as casein, albumin, and meat protein. Non-limiting examples of meat protein useful herein include a protein source selected from the group consisting of beef, pork, lamb, poultry, fish, vegetable, and mixtures thereof. The compositions may also contain other materials such as dried whey and other dairy by products.

The compositions of the present invention may further comprise a source of carbohydrate. Grains or cereals such as rice, corn, milo, sorghum, barley, alfalfa, wheat, and the like are illustrative sources. Soy protein may be particularly useful herein, for example, with respect to companion animal chews.

One or more humectants may also be utilized. Humectants may be particularly useful for extruded compositions such as, for example, chews. Examples of humectants include glycerin, sorbitol, xylitol, polyethylene glycols, propylene glycols, other edible polyhydric alcohols, and mixtures thereof. Wherein a humectant is utilized, the composition may optionally comprise from about 0.001% to about 25%, or from about 0.01% to about 20%, or from about 0.1% to about 15% of humectant, all by weight of the composition.

Optionally, the compositions herein are substantially free of rawhide. The term "substantially free of rawhide" means that the referenced composition comprises less than about 1% rawhide, preferably less than about 0.5%, and most preferably less than about 0.2% rawhide, all by weight of the composition.

Methods of the Present Invention

The methods of the present invention comprise orally administering (i.e., through ingestion) a composition of the present invention to a companion animal to provide improvement in breath odor of the companion animal, or treating oral cavity tartar (defined herein as including calculus), oral cavity plaque, periodontal disease, gingivitis, inhibition of bacterial growth in oral cavity, and combinations thereof, as applicable.

As used herein, the term "orally administering" with respect to the companion animal means that the animal ingests or a human is directed to feed, or does feed, the animal one or more compositions herein. Wherein the human is directed to feed the composition, such direction may be that which instructs and/or informs the human that use of the composition may and/or will provide the referenced benefit, for example, improvement in breath odor, treatment of oral cavity plaque or tartar, or the like. For example, such direction may be oral direction (e.g., through oral instruction from, for example, a veterinarian or other health professional), radio or television media (i.e., advertisement), or written direction (e.g., through written direction from, for example, a veterinarian or other health professional (e.g., scripts), sales professional or organization (e.g., through, for example, marketing brochures, pamphlets, or other instructive paraphernalia), written media (e.g., internet, electronic mail, or other computer-related media)), and/or packaging associated with the composition (e.g., a label present on a container holding the composition). As used herein, "written" means through words, pictures, symbols, and/or other visible descriptors. Such information need not utilize the actual words used herein, for example, "odor", "oral", "cavity", "companion", or "adapted for use", but rather use of words, pictures, symbols, and the like conveying the same or similar meaning are contemplated within the scope of this invention.

The compositions described herein may be used as a supplement to ordinary dietetic requirements or may serve as the primary food for the companion animal (and, as such, the supplements or foods may be nutritionally balanced). Administration may be on as as-needed or as-desired basis, for example, once-monthly, once-weekly, or daily (including multiple times daily). When utilized as a supplement to ordinary dietetic requirements, the composition may be administered directly to the companion animal or otherwise contacted with or admixed with companion animal food. When utilized as a companion animal food, administration will be well-known to those of ordinary skill. The amount of composition utilized may be dependent on a variety of factors, including the quality of oral health of the animal, preference of the animal as determined by the guardian of the animal or other person administering the composition, the quality of the companion animal food, and size, age, or breed or the companion animal.

Methods of Analysis

The present compositions may be utilized to enhance the oral health, or associated conditions (for example, in the case of gingivitis) of the companion animal. Various methods of demonstrating such enhancements or improvements, or other relevant methods, are well-known to those of ordinary skill in the art. As examples, the following provides illustrations of certain methods which may be used. These methods are not intended to limit the scope of the invention.

Release from Surface of Composition:

In order to be effective at least a portion of the mineral component utilized in the compositions must be dissolved in the saliva of the companion animal. In order to test for this a biscuit or treat or chew containing a known amount of mineral component which is coated on the surface of the composition is placed into a 50 mL test tube and about 5 mL of water is added. A filtering cap is placed over the top and the contents are shaken briefly (about 15 seconds). The tube is then inverted and the water containing dissolved substances passes through the filter and is collected in a separate tube ("dissolved coating") while undissolved materials are retained above the filter. The water sample is then assayed for the amount of mineral component, or for effectiveness in in vitro test systems. This is compared against the known amount of mineral component which was coated on the surface of the composition, in order to determine solubility.

Malodor Reduction:

Reduction in oral cavity malodor can be measured in accordance with a variety of techniques. An illustrative technique is the Kleinberg Salivary Sediment System Model, which is generally summarized as follows. Fresh saliva is collected from a companion animal and centrifuged to concentrate the cellular debris, microbes, food particles, and the like. A portion of the sediment is added back, then the tube is treated with control substances, with mineral component, phosphate component, or with "dissolved coating" (see *Release from Surface of Composition*, above). After times ranging from 2 to 24 hours, the odor emanating from the tube is measured organoletpically or using a Halimeter (Interscan Corp., Chatsworth, Calif.). The method is more specifically described in "The Biological Basis of Oral Malodor Formation", Kleinberg and Codpilly, Chapter 2 in Bad Breath; *Research Perspectives*, M. Rosenberg Editor, Ramot Publishing, Tel Aviv University, 1995.

Inhibition of Oral Cavity Microbial Growth:

Saliva is collected from a companion animal and diluted 1:100 in Mueller Hinton broth medium. 3 mL of this inoculum is pipetted into sterile culture tubes, and various amounts of a solution of mineral component, phosphate component, or "dissolved coating" (see *Release from Surface of Composition*, above) is added. The tubes are incubated in 5% $CO_2$ atmosphere and observed for microorganism growth after 24 or 48 hours.

Inhibition of Bioplaque Films:

This assay determines the ability of a given composition to prevent or inhibit growth of harmful organisms in plaque or of organisms which produce noxious odors in the oral cavity. Hydroxyapatite chips (simulating a tooth surface) are immersed in fresh canine or feline saliva-based medium with gentle agitation to initiate biofilm growth on the chip. The chip is continuously bathed with the saliva-based medium and intermittently treated with, control, mineral component, phosphate component, or "dissolved coating" (see *Release from Surface of Composition*, above). At the end of the experiment the biofilms are evaluated for effectiveness of the treatments. Several variations on the plaque biofilm model are available, for example as described in Guggenheim et al., "Validation of an in vitro biofilm model of supragingival plaque," *Journal of Dental Research*, Vol. 80, pp. 363-370 (2001).

Methods of Making

The presently described compositions are made according to methods which will be well known by the ordinarily skilled artisan. To illustrate, the compositions of the present invention may be prepared by mixing all components singularly or in suitable combinations together, and in water where appropriate, agitating mechanically until all of the ingredients have been solubilized, dispersed, or otherwise mixed, as applicable. Wherein certain processes such as extrusion (to form kibbles or chews, for example) or baking are utilized, such processes will be well-known in the art.

EXAMPLES

The following are non-limiting examples of the present compositions which are prepared utilizing conventional methods. The following examples are provided to illustrate the invention and are not intended to limit the scope thereof in any manner.

Example 1

A mineral component is prepared by combining 2.19 g zinc sulfate monohydrate, 2.88 g manganese chloride tetrahydrate, and 0.79 g copper sulfate pentahydrate in a mortar and pestle. The powders are finely ground and thoroughly mixed. Savory masking flavor, at an amount of 3%, by weight, is added to the mineral component. A 12 gram baked dog biscuit is painted on one side with a 30% solution of corn syrup solids glazing (N-TACK®, commercially available from National Starch and Chemical Co., Bridgewater, N.J., U.S.A). The combination of mineral component and savory masking flavor is sprinkled onto the wet glazing in an amount of 121 milligrams of the combination per biscuit, and the glazing is dried.

Example 2

Zinc sulfate monohydrate (2.20 g), manganese sulfate monohydrate (2.46 g), and copper sulfate pentahydrate (0.79 g) are combined in a mortar and pestle to a fine powder and triturated together. To this mixture is added 26.58 g granular mannitol carrier (PEARLITOL 100 SD, Roquette Corp.) using a standard pharmacy practice of ordered mixing. The granular mannitol carrier aids in masking the flavor of the mineral component and greatly enhances the dissolution of the minerals in saliva. A 4 gram extruded dog chew is painted on one side with a 30% solution of corn syrup solids glazing (N-TACK®, commercially available from National Starch and Chemical Co., Bridgewater, N.J., U.S.A). The wet side of the biscuit is pressed into the mixture of mineral component and mannitol carrier and any loose powder is gently tapped off. About 185 milligrams of material remains on the surface of the biscuit. The glazing solution is dried in a convection oven at 70° C. for about 20 minutes.

Example 3

50 grams of water is added to a beaker and stirred vigorously. 50 grams sodium polyphosphate is added, and stirring continues about 1 hour until a clear viscous solution is obtained. A 4 gram baked dog biscuit is dipped into the viscous solution and allowed to drain until about 400 mg solution remains. The biscuit is then dried in a 70° C. convection oven for about 20 minutes, and is then cooled to room temperature.

6.59 grams zinc suflate monohydrate and 7.39 grams manganese sulfate monohydrate are combined in a mortar and pestle and finely ground. 20.96 grams granular mannitol (PEARLITOL 100 SD) is added to the mineral component using the principal of ordered mixing, and mixed thoroughly by trituration.

The bottom side of the polyphosphate-coated biscuit is painted with a 30% water solution of corn syrup solids glazing (N-TACK®, commercially available from National Starch and Chemical Co., Bridgewater, N.J., U.S.A), and then the glazed side of the biscuit is pressed into a bed of the combination of mineral component and mannitol carrier. The biscuit is tapped to remove loosely held powder to leave about 67 mg powder. The biscuit is then dried in a 70° C. convection oven for about 20 minutes. Savory flavor is sprinkled on top of the powdered side of the biscuit.

Example 4

44.4 grams water is added to a beaker and stirring is started. With constant stirring, 34.7 grams GLASS H polyphosphate is added and stirring is continued until a clear solution is obtained. To this solution the following are added: 2.72 grams zinc sulfate monohydrate, 3.06 grams manganese sulfate monohydrate, and 0.98 grams copper sulfate pentahydrate. Stirring is continued until a clear, blue-tinged solution is obtained. 4 gram baked dog biscuits are dipped into the solution and allowed to drain until about 500 mg solution is adhered to each biscuit. The biscuits are dried in a 70° C. convection oven for about 30 minutes.

Example 5

48.5 grams water is added to a beaker. While stirring, 3 grams copper (II) gluconate is added. While stirring vigorously, 48.5 grams sodium polyphosphate (GLASS H) is sprinkled in, and stirring continues until a clear, blue tinted solution is obtained.

12 gram, paw-shaped dog biscuits are dipped into the solution of copper and phosphate component and allowed to drain until about 928 mg solution remains on the biscuit. Drying is carried out in a 70° C. convection oven for about 30 minutes.

A coating powder is prepared by combining 2.63 grams zinc sulfate monohydrate and 2.96 grams manganese sulfate monohydrate in a mortar and pestle. These are finely ground. 8.39 grams granular mannitol is added using the standard principal of ordered mixing, and trituration with a spatula. 2.34 grams spray-dried chicken meat and 1.26 grams spray dried chicken liver are added to the powder and mixed until uniform.

The bottom side of the biscuits are painted with a 30% water solution of corn syrup solids glazing (N-TACK®, commercially available from National Starch and Chemical Co., Bridgewater, N.J., U.S.A), and then the wet side is pressed into a bed of powder as described in the previous paragraph. The biscuits are placed powder side up on a tray and dried in a 70° C. convection oven for about 30 minutes. The total amount of powder applied per biscuit is approximately 293 milligrams.

Example 6

A biscuit which may be utilized for any of Examples 1 and 3-5 may be prepared using the following components in the indicated amounts:

| Component | Amount (by weight percent) |
| --- | --- |
| Rosemary Extract | 0.1 |
| Emulsifier | 1 |
| Vegetable Oil | 1.5 |
| Beet Pulp (from sugar beet) | 4 |
| Potassium Sorbate | 0.05 |
| Dehydrated Parsley | 0.5 |
| Meat Flavor | 0.8 |
| Wheat Germ | 5 |

| Component | Amount (by weight percent) |
| --- | --- |
| Oats | 15 |
| Corn Meal | 15 |
| Chicken By-Product Meal | 20 |
| Whole Wheat Flour | Remainder |

The components are combined, shaped as desired, and baked to form biscuits.

Example 7

A chew which may be utilized for Example 2 may be prepared using the following components in the indicated amounts:

| Component | Amount (by weight percent) |
| --- | --- |
| Sodium Tripolyphosphate | 1.8 |
| Rosemary Extract | 0.1 |
| Potassium Sorbate | 0.06 |
| Flavor | 0.6 |
| Vegetable Oil | 1.5 |
| Beet Pulp | 5 |
| Glycerin | 10 |
| Chicken by-product Meal | 10 |
| Wheat Flour | 23 |
| Soy Flour | Remainder |

The components are combined and extruded according to conventional methods as desired to form the chew. Optionally, the chew is prepared by combining all components except for the mineral component, extruding at high temperature, feeding glycerin continuously into a preconditioner until the proper consistency or texture is obtained. The product may then be cut to desired length and cooled.

The chews may then be spray-coated with a suspension of the mineral component in any fat or oil. The following technique may be illustrative: A dispersion is prepared containing 3 grams of finely powdered zinc malate and 3 grams of finely powdered manganese malate in 100 grams refined liquid chicken fat. This dispersion is sprayed onto a 25 gram chew at a rate of 0.33 grams of the dispersion per chew.

Example 8

Two kibble compositions having the following components at the approximate indicated amounts are prepared using methods which are standard in the art and are fed to dogs, each resulting in improved oral cavity health, including reduction in tartar or plaque and improved breath odor. For Example 1A, the copper source is integrated throughout the kibble, while the zinc source is coated on the surface of the kibble (along with the palatant). For Example 1B, the zinc source is integrated throughout the kibble, while the hexametaphosphate is coated on the surface of the kibble (along with the palatant).

| Component | Example 1A (Component Amount indicated as Wt %) | Example 1B (Component Amount indicated as Wt %) |
| --- | --- | --- |
| Copper Sulfate Pentahydrate | 0.03 | 0 |
| Zinc sulfate monohydrate | 0.1 | 0.15 |
| Hexametaphosphate | 0 | 0.3 |
| Palatant | 0.1 | 0.08 |
| Poultry, Poultry By-product Meal, and Fish Meal | 44 | 47 |
| Animal Fat | 8 | 6 |
| Beet Pulp and fructooligosaccharide | 2.2 | 3 |
| Salts | 2.5 | 2 |
| Vitamins and Minerals* | 1 | 1 |
| Minors | 3.5 | 4 |
| Grains (corn, sorghum, barley, rice) | Remainder | Remainder |

*Vitamins and Minerals include: Vitamin E, beta-carotene and Vitamin A, Zinc Oxide, Ascorbic Acid, Manganese Sulfate, Copper Sulfate, Manganous Oxide, Calcium Pantothenate, Biotin, Vitamin $B_{12}$, Vitamin $B_1$, Niacin, Vitamin $B_2$, Vitamin $B_6$, Vitamin $D_3$, Folic Acid.

Example 9

Two studies are conducted to measure the effects of combining a phosphate component with a mineral component in a surface-coated companion animal food. A short chain polyphosphate (pyrophosphate) is analyzed in a feline feeding model, and a long chain polyphosphate is analyzed in a canine feeding model.

A general protocol is as follows: Animals are housed at accredited facilities. All studies involve a cross-over design to evaluate products. At the start of each test period, all animals receive anesthesia followed by a thorough dental prophylaxis to remove all supra- and sub-gingival deposits. After prophylaxis, each animal is maintained on a dry diet (companion animal food) calculated to provide the appropriate energy to maintain weight for the duration of the test period. All studies have a minimum feeding period of four weeks and a maximum feeding period of nine weeks. At the end of the test period, animals are examined for presence of calculus. Following examination, a prophylaxis is performed and the animals are returned to their respective housing and assigned new diet for second period. For all oral exams, target tooth sites for canine studies include the buccal surfaces on both sides of the mouth at positions: Upper Jaw: I3, C, P2, P3, P4, and M1 and Lower Jaw: C, P2, P3, P4, and M1. Target tooth sites for feline studies include the buccal surfaces on both sides of the mouth at positions: Upper Jaw: C, P3, and P4 and Lower Jaw: C, P3, P4, and M1.

Results are as follows:

| Feline Study | N | Calculus Score | Percent Reduction |
|---|---|---|---|
| Diet 1. Diet + Pyrophosphate | 28 | 2.40 | — |
| Diet 2. Diet + Pyrophsophate + 250 ppm zinc coated on surface of diet | 28 | 2.02* | 16% |

*Diet 2 results in statistically less calculus than Diet 1.

| Canine Study | N | Calculus Score | Percent Reduction |
|---|---|---|---|
| Diet 1. Diet + GLASS H | 28 | 3.02 | — |
| Diet 2. Diet + GLASS H + 500 ppm zinc coated on surface of diet + 150 ppm copper coated on surface of diet | 28 | 2.57* | 15% |

*Diet 2 results in statistically less calculus than Diet 1.

The data shows that the combination of mineral and phosphate components reduces the growth rate of calculus in both canines and felines versus the same level of phosphate component alone.

All documents cited in the Detailed Description of the Invention are, in relevant part, incorporated herein by reference, the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An edible composition for use by a dog or cat comprising an amount of a water soluble mineral component effective for reducing malodor of the oral cavity, wherein the soluble mineral component comprises copper and one or more minerals selected from the group consisting of zinc and manganese,
   wherein at least 75% by weight of said water soluble mineral component is coated on the surface of the composition such that at least part of the mineral component is dissolved in saliva of a dog or cat during mastication; and
   wherein the edible composition comprises a nutritionally balanced dog food or cat food composition;
   wherein the edible composition is a dry composition.

2. The edible composition according to claim 1 wherein:
   a. the composition comprises at least 0.001% zinc ion, by weight of the composition;
   b. the composition comprises at least 0.0005% copper ion, by weight of the composition; and
   c. the composition comprises at least 0.0001% manganese ion, by weight of the composition.

3. The edible composition according to claim 1 wherein at least 95% of the mineral component, by weight of the mineral component, is coated on the surface of the composition.

4. The edible composition according to claim 2 comprising at least 0.02% of the mineral component, by weight of the composition.

5. The edible composition according to claim 3 wherein:
   a. the mineral component comprises a salt selected from the group consisting of zinc sulfate, zinc gluconate, zinc chloride, zinc citrate, zinc lactate, zinc malate, and mixtures thereof;
   b. the mineral component comprises a salt selected from the group consisting of copper chloride, copper gluconate, copper sulfate, copper bisglycinate, copper lactate, copper malate, copper acetate, and mixtures thereof; and
   c. the mineral component comprises a salt selected from the group consisting of manganese chloride, manganese sulfate, manganese gluconate, manganese acetate, and mixtures thereof.

6. The edible composition according to claim 5 wherein:
   a. the composition comprises from about 0.001% to about 1% zinc ion, by weight of the composition;
   b. the composition comprises from about 0.0005% to about 0.1% copper ion, by weight of the composition; and
   c. the composition comprises from about 0.001% to about 0.5% manganese ion, by weight of the composition
   wherein the soluble mineral component further comprises tin in the form of a salt selected from tin lactate, tin gluconate, tin acetate, tin sulfate, tin malate, and mixtures thereof and the composition comprises from about 0.0005% to about 0.1% tin ion, by weight of the composition.

7. The edible composition according to claim 1 further comprising pyrophosphate.

8. The edible composition according to claim 1 further comprising polyphosphate.

* * * * *